United States Patent
Auweter et al.

(10) Patent No.: US 6,271,396 B1
(45) Date of Patent: Aug. 7, 2001

(54) USE OF ORGANOSULFUR COMPOUNDS FOR EFFECTING A BATHOCROMIC SHIFT IN THE UV/VIS ABSORPTION BANDS OF CAROTENOIDS

(75) Inventors: Helmut Auweter, Limburgerhof; Heribert Bohn, Wattenheim; Dieter Horn, Heidelberg; Klaus Krämer, Landau; Joachim Paust; Horst Weiss, both of Neuhofen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/352,140

(22) Filed: Jul. 13, 1999

(30) Foreign Application Priority Data

Jul. 16, 1998 (DE) .............................................. 198 31 865

(51) Int. Cl.[7] ....................... C07C 403/02; C07D 339/04
(52) U.S. Cl. .............................................. 549/39; 585/351
(58) Field of Search ................................. 514/440, 844; 549/39; 424/401, 439, 442; 426/269; 585/351

(56) References Cited

U.S. PATENT DOCUMENTS

| 3,110,598 | 11/1963 | Mueller ................................... 99/148 |
| 4,435,427 | 3/1984 | Hoppe et al. ......................... 424/356 |
| 4,522,743 | 6/1985 | Horn et al. ............................ 252/311 |
| 5,292,538 | * 3/1994 | Paul et al. . |
| 5,350,773 | 9/1994 | Schweikert et al. .................. 514/763 |
| 5,364,563 | 11/1994 | Cathrein et al. ...................... 252/311 |
| 5,710,177 | * 1/1998 | Sauermann et al. . |

FOREIGN PATENT DOCUMENTS

| 1211911 | 8/1960 | (DE) . |
| 921306 | 3/1963 | (EP) . |
| 064193 | 11/1982 | (EP) . |
| 410236 | 1/1991 | (EP) . |
| 551638 | 7/1993 | (EP) . |
| 91/06292 | 5/1991 | (WO) . |
| 94/06310 | 3/1994 | (WO) . |
| 94/19411 | 9/1994 | (WO) . |

OTHER PUBLICATIONS

Feichtmayr et al., *Tetrahedron*, 25(22), 1969, 5383–5408.
*Chem. Abst.*, 45(1), Jan. 10, 1951, AN 372f (Abstract of DK 71108A).
*Carotenoids*, vol. 1B, 1995, p. 43–44.

* cited by examiner

*Primary Examiner*—Taofiq A. Solola
(74) *Attorney, Agent, or Firm*—Keil & Weinkauf

(57) ABSTRACT

Organosulfur compounds can be used in complexes with carotenoids for effecting a bathochromic shift in the absorption bands of carotenoids in the UV/vis spectrum. Carotenoid formulations comprising these complexes, a process for preparing these formulations and their use in the food, cosmetics and pharmaceutical sectors are described.

7 Claims, No Drawings

USE OF ORGANOSULFUR COMPOUNDS FOR EFFECTING A BATHOCROMIC SHIFT IN THE UV/VIS ABSORPTION BANDS OF CAROTENOIDS

Use of organosulfur compounds for effecting a bathochromic shift in the UV/vis absorption bands of carotenoids The invention relates to the use of organosulfur compounds in complexes with carotenoids for effecting a bathochromic shift in the absorption bands of carotenoids in the UV/vis spectrum. The invention further relates to carotenoid formulations in which these complexes are present, a process for preparing these formulations and also their use in the food, cosmetics and pharmaceutical sectors.

Carotenoids form a group of pigments having a yellow to red shade which are widespread in nature and give many foodstuffs a characteristic color. The most important representatives of this class of substances are β-carotene, β-apo-8'-carotenal, canthaxanthene, asthaxanthene, lycopene and citranaxanthene. These substances, which can be prepared synthetically, are important pigments both for the food industry and for pharmaceutical technology, for example as a replacement for synthetic dyes, and are also sometimes of great interest because of their pro-vitamin A activity and also as antioxidants.

Natural or identical-to-natural food colorants are becoming increasingly important for coloring foods. An important reason for this trend is without doubt the lack of acceptance of synthetic food colorants on the part of consumers.

When using the abovementioned carotenoids as colorants, it is possible to achieve different colors from light yellow to dark red depending on the representative of this class of substances used or depending on the carotenoid formulation used.

In order to cover a broader color spectrum by means of carotenoids, work is continually going on in this field to develop new formulations.

Thus, various methods of improving the color yields have been described, all of them having the aim of reducing the crystallite size of the active compounds and bringing it to a particle size range of less than 10 μm. Apart from milling carotenoids, as described in WO 91/06292 and WO 94/19411, these methods include, for example, the known emulsification and micronizing methods, as described, for example, in DE-A-12 11 911, EP-A-0 410 236 and EP-B-0 065 193.

EP-A-0 551 638 describes emulsions of β-carotene which are stabilized by ascorbyl palmitate as emulsifier, while WO 94/06310 describes the use of carotenoid solubilisates for coloring beverages.

It is known from "Carotenoids", Volume 1B, Birkhäuser 1995, Basle, edited by G. Britton, page 43, that the UV/vis spectra of carotenoids dissolved in carbon disulfide display a bathochromic shift of from 30 to 40 nm relative to the UV/vis spectrum of carotenoids dissolved in hydrocarbons. The carotenoids accordingly have a redder shade which is frequently desired for particular applications, for example for coloring beverages.

Owing to its highly toxic effect, for example on the nervous system, use of the inorganic carbon disulfide as, for example solvent or dispersant for carotenoids is out of the question in the food sector.

It is an object of the present invention to provide novel, stable carotenoid formulations which make it possible to achieve new shades of color and which do not have the abovementioned disadvantages of the prior art.

We have found that this object is achieved by the use of organosulfur compounds for effecting a bathochromic shift in the absorption maxima of carotenoids in the UV/vis spectrum.

Thus, it has surprisingly been found that carotenoids in complexes with organosulfur compounds display a change in their color toward redder shades, associated with a bathochromic shift in their absorption maxima.

This effect was all the more surprising since, in contrast to carbon disulfide, the organosulfur compounds used are not solvents and, in addition, have different polarities than $CS_2$.

For the purposes of the present invention, the term complexes refers in the widest sense to substances in which intermolecular interactions occur as a result of combining carotenoids and organosulfur compounds and in which the above-described shifts in the absorption maxima are observed. These can be, for example, adducts, associates, aggregates or inclusion compounds.

The bathochromic shift in the absorption maxima of the carotenoids in the UV/vis spectrum caused by the organosulfur compounds is in the range from 1 to 100 nm, preferably in the range from 2 to 60 nm, particularly preferably in the range from 3 to 50 nm. For the purposes of the present invention, the bathochromic shift is the change in the wavelength of the absorption maxima of the respective carotenoids in the complexes compared to the measured spectra of the carotenoids without addition of the organosulfur compounds used according to the present invention.

The organosulfur compounds used can be, inter alia, the following sulfur-containing natural products or derivatives thereof:

amino acids such as cystine, cysteine, N-acetylcysteine, S-propylcysteine, S-allylcysteine or methionine;

constituents of garlic, e.g. diallyl thiosulfinate, S-allylcysteine sulfoxide, vinyl dithiines, allicin;

allithiamines such as benfotiamine, fursultiamine, octotiamine or bentiamine;

glutathione and its esters, e.g. GSH monomethyl ester, GSH dimethyl ester, GSH monoethyl ester, GSH diethyl ester.

Preferred organosulfur compounds are lipoic acid and particularly preferably lipoic acid derivatives. The lipoic acid can be racemic or enantiomerically pure (R)- or (S)-lipoic acid. Examples of lipoic acid derivatives are the following compounds: $C_1-C_{20}$-alkyl lipoates, lipoic $C_1-C_{20}$-alkylamides, dihydrolipoic acid, $C_1-C_{20}$-alkyl dihydrolipoates, dihydrolipoic $C_1-C_{20}$-alkylamides, both in racemic and in optically pure form.

Examples of alkyl radicals of the esters or amides of lipoic acid or dihydrolipoic acid are branched or unbranched $C_1-C_{20}$-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

Preferred alkyl radicals are methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 2-ethylhexyl.

The carotenoids which together with the organosulfur compounds used according to the present invention can form the abovementioned complexes are the known, natural or synthetic representatives of this class, e.g. β-carotene, lycopene, bixene, zeaxanthene, cryptoxanthene, citranaxanthene, lutein, canthaxanthene, β-apo-4-carotenal, β-apo-8-carotenal, β-apo-8-carotenoic esters and astaxanthene, individually or as mixtures. Particular preference is given to using the industrially readily accessible representatives such as β-carotene, canthaxanthene, β-apo-8-carotenal, astaxanthene or lycopene, in particular β-carotene, astaxanthene and/or lycopene.

The weight ratios of carotenoids to organosulfur compounds in the complexes are in the range from 1:0.001 to 1:1000, preferably in the range from 1:0.01 to 1:100, particularly preferably in the range from 1:0.02 to 1:50, very particularly preferably in the range from 1:1 to 1:10.

The complexes can be prepared, in the simplest case, by mixing one or more carotenoids with at least one organosulfur compound, if desired in a solvent, for example in chlorinated hydrocarbons such as methylene chloride or chloroform or in an alcohol, for example isopropanol. To increase the solubility, it may be advantageous to warm the mixture briefly.

The present invention likewise provides carotenoid formulations comprising a) at least one complex of at least one carotenoid and at least one organosulfur compound and b) at least one further auxiliary or additive.

As in the above-described complexes, bathochromic shifts in the absorption maxima in the UV/vis spectrum of the carotenoids have been found in the carotenoid formulations prepared from the said complexes.

These shifts are likewise in the range from 1 to 100 nm, preferably in the range from 2 to 60 nm, particularly preferably in the range from 3 to 50 nm.

The organosulfur compounds present in the carotenoid formulations in the form of the complexes described above are, for example, the abovementioned sulfur-containing natural products.

Preferred carotenoid formulations are those comprising lipoic acid or the lipoic acid derivatives which have been described in more detail above.

The carotenoid content of the formulations of the present invention is generally from 0.01 to 25% by weight, preferably from 1 to 20% by weight, particularly preferably from 5 to 15% by weight, based on the total amount of formulation.

The content of organosulfur compounds in the formulations of the present invention is generally from 0.1 to 40% by weight, preferably from 1 to 30% by weight, particularly preferably from 2 to 25% by weight, based on the total amount of formulation.

For the purposes of the present invention, the term "carotenoid formulations" refers to solutions, solubilisates and dispersions, e.g. emulsions or suspensions, as well as dry carotenoid powders produced therefrom.

The type of carotenoid formulation determines, for example, which organosulfur compound is particularly suitable for effecting a bathochromic shift in the absorption maxima of carotenoids. It can be advantageous for the lipophilicity of the organosulfur compound to be matched to the carotenoid formulation. Thus, for example, lipophilic lipoic esters or amides are advantageous in oil-containing carotenoid formulations. In alcoholic solutions of carotenoids, on the other hand, the more polar sulfur-containing amino acids and lipoic acid or dihydrolipoic acid can also be used for the abovementioned application.

Apart from the complex(es) designated as component a), the formulations comprise at least one further auxiliary or additive, e.g. protective colloids, oils, plasticizers, antioxidants and/or emulsifiers.

Examples of protective colloids used are gelatin, fish gelatin, starch, dextrin, vegetable proteins, pectin, gum arabic, casein, caseinate or mixtures thereof. However, it is also possible to use polyvinyl alcohol, polyvinylpyrrolidone, methylcellulose, carboxymethylcellulose, hydroxypropylcellulose and alginates. For further details, see R. A. Morton, Fat Soluble Vitamins, Intern. Encyclopedia of Food and Nutrition, Vol. 9, Pergamon Press 1970, pp. 128–131. To increase the mechanical stability of, for example, the dry powder, it is advantageous to add a plasticizer such as sugar or sugar alcohols, e.g. sucrose, glucose, lactose, invert sugar, sorbitol, mannitol or glycerol, to the colloid.

The ratio of protective colloid and plasticizer to carotenoid solution is generally selected so that the end product obtained is a formulation comprising, in addition to the abovementioned carotenoids and organosulfur compounds, from 10 to 50% by weight of a protective colloid, from 20 to 70% by weight of a plasticizer, all percentages based on the dry weight of the formulation, and also, if desired, minor amounts of a stabilizer.

To increase the stability of the active compound to oxidative degradation, it is advantageous to add stabilizers such as α-tocopherol, t-butylhydroxytoluene, t-butylhydroxyanisole, ascorbic acid or ethoxyquin.

Emulsifiers which can be used are, for example, ascorbyl palmitate, polyglyceryl fatty acid esters, sorbitan fatty acid esters, propylene glycol fatty acid esters or lecithin in a concentration of from 0 to 200% by weight, preferably from 10 to 150% by weight, particularly preferably from 20 to 80% by weight, based on the carotenoid(s).

It may sometimes also be advantageous in the case of a dispersion, particularly in the case of an emulsion, to additionally dissolve a physiologically acceptable oil such as sesame oil, maize oil, cottonseed oil, soybean oil or peanut oil, esters of medium-chain fatty acids of plant origin or else fish oils such as mackerel, sprat or salmon oil in the organic phase in a concentration of from 0 to 500% by weight, preferably from 10 to 300% by weight, particularly preferably from 20 to 100% by weight, based on the carotenoid(s); this oil is then precipitated in extremely finely divided form together with the active compounds and the additives mentioned on mixing with the aqueous phase.

Apart from the components a) and b), the carotenoid formulations of the present invention can comprise at least one further active compound in concentrations of from 0.01 to 40% by weight, preferably from 0.1 to 30% by weight, particularly preferably in concentrations of from 0.5 to 20% by weight.

These active compounds can be, for example, the following:

vitamins, e.g. vitamin A, vitamin A acetate, vitamin A palmitate, riboflavin, vitamin $B_{12}$, ascorbic acid, nicotinic acid, nicotinamide, pyridoxine hydrochloride, vitamin $D_3$, tocopherol, tocopherol acetate, tocotrienol, vitamin K, thiamine, calcium pantothenate, biotin, folic acid, folic acid derivatives such as tetrahydrofolic acid, 5-methyltetrahydrofolic acid, 10-formyltetrahydrofolic acid or 5-formyltetrahydrofolic acid;

compounds having a vitamin or coenzyme character, e.g. choline chloride, carnitine, taurine, creatine, ubiquinones, S-methylmethionine, S-adenosylmethionine;

polyunsaturated fatty acids, e.g. linoleic acid, linolenic acid, arachidonic acid, eicosapentaenic acid, docosahexaenic acid.

The preparation of the carotenoid formulations is carried out in a manner known per se. Thus, for example, solubilisates or emulsions can be prepared as described in U.S. Pat. No. 4,435,427 or EP-A-0 551 638. The preparation of carotenoid dispersions and their conversion into a dry powder is described, for example, in EP-A-0 065 193 and EP-A-0 410 236.

The alcohols used for the precipitation are, for example, methanol, ethanol, n-propanol, isopropanol, n-butanol, tert-butanol, preferably methanol or ethanol. Suitable ketones are acetone, methyl ethyl ketone, diethyl ketone, preferably acetone. As cyclic ether, preference is given to using tetrahydrofuran.

A preferred method of preparation is to dissolve a carotenoid together with an organosulfur compound and further auxiliaries or additives described above in a water-miscible solvent, for example methanol, ethanol, n-propanol, isopropanol, n-butanol, tert-butanol, acetone, methyl ethyl ketone, diethyl ketone or tetrahydrofuran, with dissolution time, dissolution temperature, pressure and energy input by stirring or static mixing being matched to the solubility properties of the carotenoid and the organosulfur compound. This solution can then be turbulently mixed with an aqueous phase, thus precipitating the carotenoid and the organosulfur compound together in the form of nanosize particles. The aqueous phase generally comprises a protective colloid and can also comprise further auxiliaries and additives. The nanosize dispersion obtained in this way can be concentrated and converted by known methods, for example by means of spray drying, into a dry powder.

A further possible way of producing the dry powder according to the present invention is to dissolve a carotenoid together with an organosulfur compound and, if desired, further auxiliaries or additives in a water-immiscible solvent, for example hexane, cyclohexane, toluene, methylene chloride, chloroform or ethyl acetate. This solution can then be emulsified in an aqueous phase. The aqueous phase generally comprises an emulsifier and can additionally comprise further auxiliaries and additives. Solvent and water can subsequently be distilled off, thus precipitating the carotenoid and the organosulfur compound together in the form of nanosize particles. The concentrated dispersion obtained in this way can subsequently be likewise converted into a dry powder.

The carotenoid formulations of the present invention are suitable, inter alia, as additives for producing nutrient supplement preparations for humans and animals and for producing pharmaceutical and cosmetic preparations.

Owing to their good dispersibility in cold water, the dry powders are very useful as food colorants, for example for soft drinks. They can also be added to other foods, for example milk products such as yogurt, mixed milk drinks or dairy ice cream as well as custard powders or cake mixes.

The following examples illustrate the use according to the present invention of the organosulfur compounds for effecting a bathochromic shift in the UV/vis absorption bands of carotenoids.

EXAMPLE 1

25 mg of astaxanthene were mixed with 10 g of (R,S)-dihydrolipoic acid and stirred vigorously at 40° C. for 60 minutes. After cooling to room temperature, the slightly turbid mixture was filtered through a 0.2 μm filter and transferred to a 1 cm cell for measurement of the UV/vis absorption spectrum.

The absorption spectrum, measured in the range from 350 to 650 nm, displayed a maximum at 500 nm. Compared to the reference spectrum of astaxanthene dissolved in cyclohexane ($\lambda_{max}$=474 nm), the bathochromic shift was 26 nm.

EXAMPLE 2

25 g of astaxanthene, 75 g of the methyl ester of (R)-alphalipoic acid, 2 g of ascorbyl palmitate and 7.7 g of ethoxyquin were made up into a suspension in a solvent mixture of 450 g of isopropanol and 400 g of tetrahydrofuran and stirred vigorously for 30 minutes at room temperature by means of an Ultra-Turrax. The aqueous phase was made up as follows: 88 g of gelatin B 200 Bloom, 42 g of Gelita Sol P, 146 g of sucrose and 5.01 g of preservative were dissolved in 14 l of distilled water, after which the pH of the solution was increased to from 5 to 8.5 by means of 52 ml of 1 M NaOH. At a temperature of 139° C. and a pressure of 60 bar, the suspension was converted into a molecularly disperse solution and precipitated by turbulent mixing with the aqueous phase.

Distilling of the solvents and the water and subsequent double emulsification gave a dry powder having an astaxanthene content of 7% by weight and a methyl lipoate content of 21% by weight. The dry powder redispersed in water had a particle size of 380 nm and an E1/1 value of 89. The bathochromic shift compared to a reference formulation without methyl lipoate was 4 nm.

We claim:

1. A process for effecting a bathochromic shift in the UV/vis absorption bands of caretonoids which consists essentially of forming a complex of a carotenoid with an organosulfur compound.

2. The process of claim 1 wherein the bathochromic shift in the absorption maximum in the UV/vis spectrum of from 1–100 nm.

3. The process of claim 1 wherein the carotenoid is β-carotene, lycopene, bixene, zeaxanthene, cryptoxanthene, citranaxanthene, lutein, canthaxanthene, β-apo-4-carotenal, β-apo-8-carotenal, β-apo-8-carotenoic esters or astaxanthene, or mixtures thereof.

4. The process of claim 1 wherein the organosulfur compound is cystine, cysteine, N-acetylcysteine, S-propylcysteine, S-allylcysteine or methionine, diallyl thiosulfinate, S-allycysteine sulfoxide, vinyl dithiines, allicin, benfotiamine fursultiamine, octotiamine, bentiamine, glutathione and/or its esters, lipoic acid and/or a lipoic acid group containing compounds or mixtures thereof.

5. The process of claim 4, wherein the organosulfur compound is lipoic acid and/or a lipoic acid group containing compound.

6. The process of claim 1 wherein the complex is formed by dispersing one or more carotenoid and one or more organosulfur sulfur compound in water in water or an aqueous protective colloid and, optionally, drying this dispersion.

7. The process off claim 6 wherein the carotenoid and the organosulfur compound is dissolved in a water-miscible organic solvent prior to the dispersion step.

* * * * *

UNITED STATES PATENT AND TRADEMARK OFFICE
CERTIFICATE OF CORRECTION

PATENT NO. : 6,271,396 B1
DATED : August 7, 2001
INVENTOR(S) : Auweter et al.

It is certified that error appears in the above-identified patent and that said Letters Patent is hereby corrected as shown below:

<u>Column 6,</u>
Line 56, delete "in water".
Line 59, "off" should be -- of --.

Signed and Sealed this

Twenty-ninth Day of January, 2002

Attest:

Attesting Officer

JAMES E. ROGAN
Director of the United States Patent and Trademark Office